(12) United States Patent
Kondri et al.

(10) Patent No.: US 6,465,424 B1
(45) Date of Patent: Oct. 15, 2002

(54) ANTI-ANGIOGENIC AGENT AND METHOD FOR INHIBITING ANGIOGENESIS

(75) Inventors: Mohammad Eghtedarzadeh Kondri, New Hope, PA (US); Richard-Weidong Ji, Lawrenceville, NJ (US); Pamela A. Trail, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/483,846

(22) Filed: Jan. 17, 2000

Related U.S. Application Data

(60) Provisional application No. 60/120,371, filed on Feb. 17, 1999.

(51) Int. Cl.$^7$ ................................................. A01N 37/18
(52) U.S. Cl. .................................. 514/2; 514/2; 514/12; 514/21; 514/411; 530/300; 530/350; 435/68.1; 435/69.1; 424/94.64
(58) Field of Search .......................... 514/12, 411, 21, 514/2; 435/68.1, 69.1; 424/94.64; 530/350, 300

(56) References Cited

U.S. PATENT DOCUMENTS

| | | | |
|---|---|---|---|
| 5,639,725 A | 6/1997 | O'Reilly et al. | 514/12 |
| 5,733,876 A | 3/1998 | O'Reilly et al. | 514/12 |
| 5,801,146 A | 9/1998 | Davidson | 514/12 |
| 5,945,403 A | 8/1999 | Folkman et al. | 514/21 |
| 5,972,896 A * | 10/1999 | Davidson | 514/18 |
| 5,981,484 A * | 11/1999 | Davidson | 514/12 |
| 5,981,568 A | 11/1999 | Kunz et al. | 514/411 |
| 6,024,688 A * | 2/2000 | Folkman et al. | 574/12 |
| 6,057,122 A * | 5/2000 | Davidson | 435/68.1 |

FOREIGN PATENT DOCUMENTS

| | | | |
|---|---|---|---|
| WO | WO 91/18989 | * | 12/1991 |

OTHER PUBLICATIONS

Gross et al., Journal of the National Cancer Institute, 1993, 85 (2), 121–131.
Kim et al., Nature, 1993, 362, 841–844.
O'Reilly et al., Cell, 1994, 79, 315–328.
O'Reilly et al., Nature Medicine, 1996, 2 (6), 689–692.
Wu et al., Biochemical and Biophysical Research Communications, 1997, 236, 651–654.
Cao et al., J. Clin. Invest., 1998, 101 (5), 1055–1063.
Cao et al., J. Biol. Chem., 1996, 271 (46), 29461–29467.
Ji et al., FASEB Journal, 1998, 12 (15), 1731–1738.
Ji et al., Biochemical and Biophysical Research Communications, 1998, 247, 414–419.
Cao et al., Journal of Biological Chemistry, 1997, 272 (36), 22924–22928.

* cited by examiner

*Primary Examiner*—Karen Cochrane Carlson
*Assistant Examiner*—Hope A. Robinson
(74) *Attorney, Agent, or Firm*—Joan E. Switzer; Christopher A. Klein

(57) ABSTRACT

The present invention relates to compositions that inhibit the proliferation and migration of endothelial cells. The compositions contain a pre-activation domain ("PAD") from plasminogen, or a biologically active fragment thereof, and at least one kringle region from plasminogen, or a biologically active portion thereof. The compositions are useful to treat angiogenic associated disorders.

9 Claims, 1 Drawing Sheet

Schematic diagram of K1-5 of human plasminogen. (Abbreviations: K-kringle; PAD-K1-5: kringle 1-5 with pre-activation domain of human plasminogen)

Comparison of inhibitory activities of endothelial cell migration among recombinant PAD-K1-5, angiostatin (K1-4), and K5 of human plasminogen (Abbreviations: AST-angiostatin)

SEQUENCE LISTING

```
<160> NUMBER OF SEQ ID NOS:  8

<210> SEQ ID NO 1
```

-continued

```
<211> LENGTH: 77
<212> TYPE: PRT
<213> ORGANISM: Homo sapiens

<400> SEQUENCE: 1

Glu Pro Leu Asp Asp Tyr Val Asn Thr Gln Gly Ala Ser Leu Phe Ser
  1               5                  10                  15

Val Thr Lys Lys Gln Leu Gly Ala Gly Ser Ile Glu Glu Cys Ala Ala
             20                  25                  30

Lys Cys Glu Glu Asp Glu Glu Phe Thr Cys Arg Ala Phe Gln Tyr His
         35                  40                  45

Ser Lys Glu Gln Gln Cys Val Ile Met Ala Glu Asn Arg Lys Ser Ser
     50                  55                  60

Ile Ile Ile Arg Met Arg Asp Val Val Leu Phe Glu Lys
 65                  70                  75

<210> SEQ ID NO 2
<211> LENGTH: 35
<212> TYPE: DNA
<213> ORGANISM: Homo sapiens

<400> SEQUENCE: 2
gcggatccat gaaagtgtat ctctcagagt gcaag                              35

<210> SEQ ID NO 3
<211> LENGTH: 38
<212> TYPE: DNA
<213> ORGANISM: Homo sapiens

<400> SEQUENCE: 3
gcggatcctc actattctgt tcctgagcat tttttcag                           38

<210> SEQ ID NO 4
<211> LENGTH: 33
<212> TYPE: DNA
<213> ORGANISM: Homo sapiens

<400> SEQUENCE: 4
gcggatcgat ggggatccga agaagactgt atg                                33

<210> SEQ ID NO 5
<211> LENGTH: 42
<212> TYPE: DNA
<213> ORGANISM: Homo sapiens

<400> SEQUENCE: 5
gtaccagctg cagatctcga gctactaagg ggccgcacac tg                      42

<210> SEQ ID NO 6
<211> LENGTH: 57
<212> TYPE: DNA
<213> ORGANISM: Homo sapiens

<400> SEQUENCE: 6
cctcctcttc agcagagtcg actccaagct ttactaaggg gccgcacact gagggac      57

<210> SEQ ID NO 7
<211> LENGTH: 66
<212> TYPE: DNA
<213> ORGANISM: Homo sapiens

<400> SEQUENCE: 7
```

-continued

```
gtatacattt cttacatcta tgcggatcga tggggatccg agcctctgga tgactatgtg      60
aatacc                                                                  66

<210> SEQ ID NO 8
<211> LENGTH: 69
<212> TYPE: DNA
<213> ORGANISM: Homo sapiens

<400> SEQUENCE: 8
gtatacattt cttacatcta tgcggatcga tggggatcct tatttgaaaa gaaagtgtat      60
ctctcagag                                                              69
```

ANTI-ANGIOGENIC AGENT AND METHOD FOR INHIBITING ANGIOGENESIS

CROSS-REFERENCE TO RELATED APPLICATIONS

This application claims the benefit of U.S. Provisional Application No. 60/120,371 filed Feb. 17, 1999.

FIELD OF THE INVENTION

The present invention relates to compositions useful to inhibit angiogenesis, including proliferation, migration and tube formation. The compositions comprise at least one kringle region, preferably from plasminogen, plus the upstream pre-activation domain of plasminogen. The compositions of the present invention are capable of inhibiting angiogenesis related diseases and modulating angiogenic processes.

BACKGROUND OF THE INVENTION

As used herein, the term "angiogenesis" means the generation of new blood vessels into tissue or organ. Under normal physiological conditions, humans or animals undergo angiogenesis only in very restricted situations. For example, angiogenesis is normally observed in wound healing, fetal and embryonic development and formation of the corpus luteum, endometrium and placenta. The term "endothelium" means a thin layer of flat endothelial cells that line serous cavities, lymph vessels, and blood vessels.

Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessels, where the endothelial cells undergo mitosis and proliferation. The endothelial sprouts merge with each other to form capillary loops, creating new blood vessels.

Pathological angiogenesis occurs in a number of disease states, for example, tumor metastasis and abnormal growth by endothelial cells, and supports the pathological damages seen in these conditions. The diverse pathological disease states in which abnormal angiogenesis is present have been grouped together as "angiogenic dependent" or "angiogenic associated" disorders. For a review of angiogenesis and its relation to tumor growth, see PCT publication WO 95/29242 and references cited therein, hereby incorporated by reference in its entirety.

Angiogenesis is tightly regulated by both positive and negative signals. Angiogenic stimulators, such as fibroblast growth factor (FGF) and vascular endothelial growth factor (VEGF), are potent mitogens for endothelial cell proliferation and strong chemoattractants for endothelial cell migration. These positive regulators can promote neovascularization to sustain the expansion of both primary and metastatic tumors (Gross, J. L. et. al., (1993) *J. Natl. Cancer Inst.* 85(2):121–131; Kim, K. J. et. al., (1993) *Nature* 362(6243):841–844). Among the negative regulators described to date, Angiostatin ranks as one of the most effective endogenous inhibitors of angiogenesis (O'Reilly, M. S. et. al., (1994) *Cell* 79:315–328; O'Reilly, M. S. et. al., (1996) *Nat. Med.* 2:689–692; Wu, Z. et. al., (1997) *Biochem. Biophys. Res. Commun.* 236:651–654). Angiostatin comprises an internal fragment of plasminogen and consists of four triple-looped kringle domains constrained by three disulfide bonds. Angiostatin was shown to inhibit endothelial cell proliferation in vitro and to suppress growth factor-induced angiogenesis in vivo (O'Reilly (1994), supra). Inhibition of angiogenesis by treatment with angiostatin results in significant suppression of tumor growth in both murine and human tumor models (O'Reilly (1994); O'Reilly (1996); Wu (1997), supra).

Angiostatin has been described as a potent angiogenesis inhibitor that could markedly suppress the growth of a variety of tumors, including carcinomas of lung, prostate, colon, and breast (Cao, Y. et. al., (1998) *J. Clin. Invest.* 101(5): 1055–1063; O'Reilly, et. al., (1996) supra; O'Reilly, et. al., (1994) supra).

The individual kringle domains of angiostatin have distinct anti-proliferative and anti-migratory activities toward endothelial cells (Cao, Y. et. al., (1996) *J Biol. Chem.* 271:29461–29467; Ji, W. R. et. al., (1998) *FASEB Jrnl* 12(15):1731–1738). It has been documented that the first three kringles of angiostatin exhibit potent inhibitory activities on endothelial cell proliferation whereas kringle 4 has a marginal effect. It was also shown that the intact kringle structure is essential for the anti-proliferative activities of angiostatin.

The kringle 5 of human plasminogen displays high structural similarity and about 50% sequence identity to the four kringles of angiostatin. Kringle 5 was reported to inhibit bFGF-elicited endothelial cell growth in a dose-dependent manner (Ji, W. R. et. al., (1998) *Biochem Biophys Res Commun.* 247(2):414–419; Cao, Y. et. al., (1997) *J. Biol. Chem.* 272:22924–22928). These data suggest that kringle 5, like angiostatin, may have potent anti-angiogenic activities.

The pre-activation domain of plasminogen is known to be essential for the stability of plasminogen.

SUMMARY OF THE INVENTION

In accordance with the present invention, compositions are provided comprising at least one kringle region from plasminogen and the pre-activation domain of plasminogen ("PAD"). The new molecules, which include the 5 kringle domains of plasminogen, or fragments thereof, including but not limited to PAD-K1–4, PAD-K1–3, PAD-K1–2, PAD-K2–3, PAD-K1, and PAD-K5, or any combination thereof, optionally in a monovalent or bivalent Ig-linked form, including fusion molecules, are encompassed herein. Applicants herein provide evidence that compositions comprising at least one kringle region plus the PAD show superior results over Angiostatin (K1–4 of plasminogen), and the K5 region alone.

The present invention also comprises a process for making anti-angiogenic compounds, wherein the anti-angiogenic compounds comprise at least one kringle region from plasminogen, the method comprising associating the PAD of plasminogen with said at least one kringle region from plasminogen. The novel method provides a way to recombinantly manufacture active anti-angiogenic compounds comprising, for example, Angiostatin (K1–4 of plasminogen), K5, K1–5, or any other combination of kringle regions from plasminogen.

The present invention provides methods and compositions for treating diseases and processes mediated by undesired and uncontrolled angiogenesis by administering to a human or animal a composition comprising at least one kringle region plus the PAD of plasminogen. The present invention is particularly useful for treating, or for repressing the growth of, tumors. Administration of compositions of the present invention to a human or animal with prevascularized metastasized tumors will prevent the growth or expansion of those tumors.

The methods of the present invention encompass the use of a composition comprising at least one kringle region plus the PAD of plasminogen. Additionally, the methods of the present invention encompass the use of two or more compositions, wherein each composition comprises at least one klingle region plus the PAD of plasminogen, said compositions administered simultaneously or sequentially.

All references cited herein, whether supra or infra, are hereby incorporated by reference in their entirety.

DETAILED DESCRIPTION OF THE INVENTION

Figure 1:
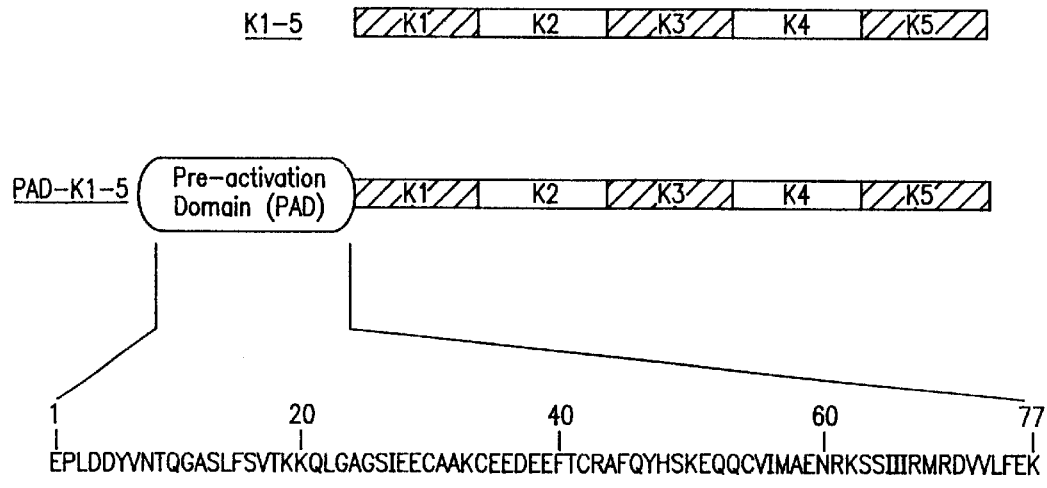
FIG. 1 is a schematic diagram of K1–5 of human plasminogen. (Abbreviations: "K"—kringle; "PAD-K1–5"—kringles 1–5 from plasminogen with pre-activation domain ("PAD") of human plasminogen).
Figure 2:
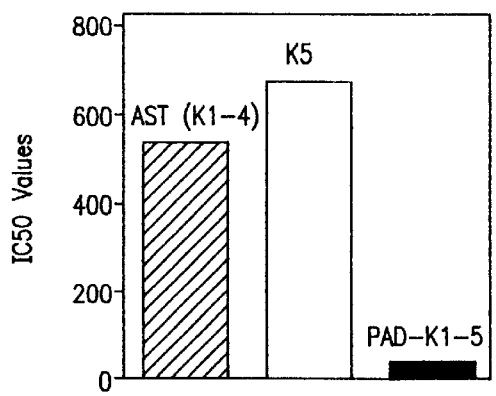
FIG. 2 shows the results of a comparison of inhibitory activities of endothelial cell migration between recombinant PAD-K1–5, Angiostatin (K1–4), and K5 of human plasminogen. (Abbreviations: "AST"—Angiostatin).

Angiostatin has been described as a potent angiogenesis inhibitor that can markedly suppress the growth of a variety of tumors, including carcinomas of lung, prostate, colon, and breast. Angiostatin and the sequences of mouse, human, rhesus monkey, porcine and bovine plasminogen are given in U.S. Pat. No. 5,639,725, the disclosure of which is incorporated herein by reference in its entirety.

The kringle 5 of human plasminogen displays high structural similarity and about 50% sequence identity to the four kringles of angiostatin. Kringle 5 was reported to inhibit bFGF-elicited endothelial cell growth in a dose-dependent manner. These data suggest that kringle 5, like angiostatin, may have potent anti-angiogenic activities.

It is known that the pre-activation domain ("PAD") of plasminogen is essential for the stability of plasminogen. The PAD of plasminogen comprises all or a portion of the following amino acid sequence (SEQ ID NO: 1):

EPLDDYVNTQ GASLFSVTKK QLGAGSIEEC AAKCEEDEEF
TCRAFQYHSK EQQCVIMAEN RKSSIIRMR DVVLFEK

The present invention for the first time presents evidence that a molecule that comprises the PAD of plasminogen plus at least one kringle region from plasminogen (including Angiostatin, K1, K2, K3, K4, K5, or any combination of K1–K5) exhibits superior angiogenesis inhibition over Angiostatin alone and/or kringle 5 alone.

Compositions are provided comprising the PAD from plasminogen and at least one kringle region. For purposes of the present invention, the designation "PAD-K" is meant to cover the PAD of plasminogen plus any kringle region, or combination of kringle regions, from plasminogen. The PAD and at least one kringle region (or biologically active fragment or portion thereof) may be disassociated, but are preferably joined into one molecule. Additionally, the PAD and kringle region(s) may be joined together in any order. For example, encompassed within the present invention are PAD-K molecules comprising a PAD upstream from one or more kringle regions, molecules comprising a PAD downstream from one or more kringle regions, and molecules wherein a PAD is located between two or more kringle regions.

The source plasminogen (i.e., the plasminogen from which the kringle region(s) is/are derived) may be from the same species (e.g., human) or from different species. One or more kringle regions from plasminogen, or biologically active portion thereof, may be derived, for example, from murine plasminogen, human plasminogen, Rhesus plasminogen, porcine plasminogen, canine plasminogen, or bovine plasminogen. Preferably, if more than one kringle region is attached to the PAD from plaminogen, the kringle regions are derived from the same species.

Additionally, more than one PAD-K compound may be administered in the same composition, or they may be administered in separate compositions. If separate compositions are used, the compositions may be administered simultaneously or sequentially.

Also encompassed within the scope of the present invention are variations of the PAD and kringle fragments that may be used together, including biologically active fragments or either the PAD or kringle region, and biologically active analogs involving amino acid deletions, additions and/or substitutions. "Biologically active fragment" includes fragments of PAD and/or a kringle region(s) that maintain the same biological activity of the PAD and/or kringle region from which the fragment is derived. "Biologically active analogs" includes variations of PAD and/or kringle region(s) that do not materially alter the biological activity (i.e., anti-angiogenic activity) of the PAD and/or kringle fragment from which the analog is derived. Included within the scope of the invention are changes made to the PAD and/or kringle fragment(s) that increase anti-angiogenic activity.

Preferred analogs include the PAD and/or kringle region (s) fragment(s) whose sequences differ from the wild-type sequence by one or more conservative amino acid substitutions or by one or more non-conservative amino acid substitutions, deletions or insertions which do not abolish the biological activity of the molecules. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

TABLE 1

Conservative amino acid replacements

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |

TABLE 1-continued

Conservative amino acid replacements

| For Amino Acid | Code | Replace with any of: |
|---|---|---|
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or γ amino acids.

The PAD and kringle region(s) useful in the present invention may be obtained by synthetic means, i.e., chemical synthesis of the polypeptide from its component amino acids, by methods known to those of ordinary skill in the art. For example, the solid phase procedure described in Houghton et al., (1985) *Proc. Natl. Acad. Sci.* 82:5131–5135 may be employed. The polypeptides may be obtained by production in prokaryotic or eukaryotic host cells expressing a DNA sequence coding for all or part of the desired fragment, or by in vitro translation of the mRNA encoded by a DNA sequence coding for the desired peptide. Techniques for the production of a kringle region and the PAD from plasminogen are known in the art, and are described herein.

The PAD and kringle region(s) produced in this manner may then be isolated and purified to some degree using various protein purification techniques. For example, chromatographic procedures such as ion exchange chromatography, gel filtration chromatography and immunoaffinity chromatography may be employed. The PAD and kringle region(s) may be produced alone and associated later, or may be produced as a single fusion molecule.

If the polypeptides of the invention (i.e., PAD, one or more kringle regions, or PAD-K molecule) are made through recombinant techniques, the DNA sequences useful to prepare the polypeptides of the invention can be obtained using various methods well known to those of ordinary skill in the art. The molecules described in the examples below were manufactured according to the methods described in Kondri, et al., (1997) *BioTechniques* 23(5):830–33, Ji, et al., (1998) *Biochem. Biophys. Res. Commun.* 247:414–419; and Ji, et al., (1998) *FASEB Jrnl* 12(15):1731–1738. The expression vectors can be partly or wholly synthesized chemically and/or partly or wholly prepared through genetic engineering techniques. Fragments can be sequentially ligated (via appropriate terminal restriction sites or complementary terminal sequences) so as to form the correct linear sequence of nucleotides.

The PAD-K molecules of the present invention can be manufactured using a single construct that encodes the PAD and at least one kringle region from plasminogen, or using multiple constructs encoding the PAD and at least one kringle region from plasminogen (i.e., one construct encoding the PAD and additional construct(s) encoding the at least one kringle region). By following the present invention one is able to recombinantly manufacture a stable anti-angiogenic compound comprising at least one kringle region from plasminogen (or a biologically active fragment or analog thereof).

Encompassed within the invention is a method of producing a PAD-K molecule, or a variant thereof, comprising the steps of:

a) inserting a nucleic acid sequence encoding the PAD of plasminogen (or biologically active fragment thereof) and at least one kringle region from plasminogen (or a biologically active fragment thereof) into an appropriate expression vector;

b) transfecting said expression vector into an appropriate transfection host cell(s), c) growing said transfected host cell(s) in an appropriate culture media, and d) purifying the PAD-K molecule from said culture media.

Encompassed within the present invention are methods of producing a PAD-K molecule wherein a single nucleic acid sequence encodes the PAD and at least one kringle region from plasminogen, or wherein two or more nucleic acid sequences are used encoding the PAD from plasminogen and the said at least one kringle region from plasminogen.

Expression vehicles of the invention for production of the anti-angiogenic polypeptides of the invention include plasmids or other vectors. In general, such vectors contain control sequences that allow expression in various types of hosts. Suitable expression vectors containing the desired coding and control sequences may be constructed using standard recombinant DNA techniques known in the art, many of which are described in Sambrook et al. (1989), *Molecular Cloning: A Laboratory Manual*, $2^{nd}$ edition, Cold Spring Harbor Laboratory, Cold Spring Harbor, N.Y.

An expression vector as contemplated by the present invention is capable of directing the replication of the vector in bacteria, yeast, insect, and/or mammalian cells. One class of vectors utilizes yeast DNA elements that provide autonomously replicating origins such as the yeast 2μ element or ARS1 sequence which yield extrachromosomal plasmids. A second class of vectors relies upon the integration of the desired gene sequences into the host cell chromosome. The vectors may also incorporate a bacterial origin of replication. Suitable bacterial origins of replication include, for example, the ColE1, pSC101 and M13 origins of replication.

Expression vectors useful of the present invention typically contain a promoter located 5' to (i.e., upstream of) the DNA sequence to be expressed, and a transcription termination sequence located 3' to (i.e., downstream of) the sequence to be expressed. Suitable promoters include, for example, the yeast ADH1 promoter. The promoter sequence may also be inducible, to allow modulation of expression (e.g., by the presence or absence of nutrients or other inducers in the growth medium). Examples include the yeast GAL1, CUP1, and MET25 promoters. Suitable termination sequences include, for example, the yeast CYC1 termination and polyadenylation sequences.

The expression vectors may also include other regulatory sequences for optimal expression of the desired product. Such sequences include secretory leader sequences, which provide for secretion of the expressed product or direct membrane localization, and restriction enzyme recognition sequences, which provide sites for cleavage by restriction endonucleases. All of these materials are known in the art and most are commercially available.

A suitable expression vector may also include marking sequences, which allow phenotypic detection and/or selection of transformed yeast or bacterial cells. Such a marker may provide prototrophy to an auxotrophic host (e.g., amino acid biosynthetic genes), biocide resistance or supersensitivity (e.g., antibiotic resistance) or a phenotypically detectable signal (e.g., fluorescence). The selectable marker gene can be either directly linked to the DNA gene sequences to be expressed, or introduced into the same cell by transformation. Examples of yeast selectable markers include *Basidium pullulans* AUR1-C gene, the *S. cerevisiae* URA3 or LEU2 genes and the like. Examples of bacterial selectable markers include the ampicillin resistance gene. A preferred vector is pYESII, containing the ColE1 and $2\mu$ origins of replication, the yeast URA3 and bacterial amp$^R$ genes, and the yeast GAL1 promoter sequence (Invitrogen).

In a further alternative, the constructs may be introduced into a cell by transformation in conjunction with a gene allowing for selection where the construct will become integrated into the host genome or persist episomally. Usually, the construct will be part of a vector having homologous sequences for integration or a replication system recognized by the host cell.

The compositions of the present invention, comprising the PAD from plasminogen and at least one kringle region of plasminogen (or a biologically active fragment or analog thereof), are useful to treat angiogenic-dependent or angiogenic-associated disorders. The present invention includes the method of treating an angiogenic-dependent or angiogenic-associated disorder with an effective amount of a composition comprising a PAD-K. As described above, a single composition comprising at least one PAD-K, or separate compositions (a first comprising a PAD-K and a second comprising the same or a different PAD-K) may be administered simultaneously or sequentially.

Angiogenic-dependent and/or angiogenic-associated disorders includes, but are not limited to, solid tumors, blood born tumors such as leukemias; tumor metastasis; benign tumors, for example, hemangiomas, acoustic acuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. The compositions of the present invention are useful in treatment of disease of excessive or abnormal stimulation of endothelial cells. These disorders include, but are not limited to, intestinal adhesions, atherosclerosis, scleroderma, and hypertrophic scars, i.e., keloids. The compositions can also be used as birth control agents by preventing vascularization required for embryo implantation.

The compositions and methods of the present invention may be used in combination with other compositions and procedures for the treatment of angiogenic-dependent or angiogenic-associated disorders. For example, a tumor may be treated conventionally with surgery, radiation or chemotherapy, and then compositions comprising a PAD-K as disclosed herein may be subsequently administered to the patient to extend the dormancy of micrometastases and to stabilize any residual primary tumor.

The present invention also provides pharmaceutical (i.e., therapeutic) compositions comprising a PAD-K (or a biologically active fragment or analog thereof), optionally in combination with at least one additional active compound, and any pharmaceutically acceptable carrier, adjuvant or vehicle. "Additional active compounds" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, incorporated into a composition of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS"), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the compositions of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compositions of the present invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions comprising a PAD-K, or, particularly in the case of extended release, by the use of devices such as subcutaneous implants or osmotic pumps. The present compositions may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compositions with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the active compounds (i.e., the PAD-K).

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combination, and severity of the particular condition. Preferred subjects for treatment include animals, most preferably mammalian species such as humans, and domestic animals such as dogs, cats and the like, subject to angiogenic associated disorders.

The compositions of the present invention may be employed alone or in combination with other suitable therapeutic agents useful in the treatment of angiogenic associated disorders, such as angiogenesis inhibitors other than those of the present invention, antiinflammatories, antiproliferatives, chemotherapeutic agents, immunosuppressants, and antimicrobials.

Other therapeutic agents, when employed in combination with the compositions of the present invention, may be used, for example, in those amounts indicated in the Physicians' Desk Reference (PDR) or as otherwise determined by one of ordinary skill in the art.

The following examples are further illustrative of the present invention. These examples are not intended to limit the scope of the present invention, and provide further understanding of the invention.

EXAMPLE 1

Gene Construction, Expression, and Purification of Recombinant Human Angiostatin, K5, K1–5 and PAD-K1–5

The compounds described herein (i.e., Angiostatin, K5, K1–5, PAD-K1–5, or any other PAD-K molecule comprising at least one kringle region from plasminogen), were constructed by following known PCR and homologous recombination methods known in the art, as described in Kondri, et al., (1997) *BioTechniques* 23(5):830–33; Ji, et al., (1998) *Biochem. Biophys. Res. Commun.* 247:414–419; and Ji, et al., (1998) *FASEB Jrnl* 12(15):1731–1738.

For example, the human Angiostatin cDNA was amplified from a human plasminogen cDNA template (American Type Culture Collection, Rockville, Md.) by standard polymerase chain reaction (PCR) with the following two primers:

5'-GCGGATCCATGAAAGTGTATCTCTCAGAGT
   GCAAG                                   (SEQ ID NO:2)

(forward primer for residue 98–458); and

5'-GCGGATCCTCACTATTCTGTTCCTGAGCATTT
   TTTCAG                                  (SEQ ID NO:3)

(reverse primer for residue 98–458).

The amplified cDNA fragment was ligated into the BamHI site of the pMelBacA vector (In Vitrogen, San Diego, Calif.). The Angiostatin cDNA plasmid was then co-transfected into Sf9 cells with viral BaculoGold™ DNA (PharMingen, San Diego, Calif.). Briefly, 1×10⁶ Sf9 cells were seeded in a T25 tissue culture flask and incubated at 27° C. with 1 ml of the transfection solution containing 2 µg of transfer vector DNA, 0.5 µg of BaculoGold™ DNA, and 6 µl of Cellfectin (Gibco BRL, Gaithersburg, Md.). The transfection solution was removed 4 hours post-transfection and replaced with 3 ml of Sf900II medium (Gibco BRL, Gaithersburg, Md.). Four days after incubation, the viral supernatant was harvested and individual clones were identified by limiting dilution. The clone with the highest protein expression, as determined by SDS-PAGE/Coomassie blue staining, was amplified in Sf9 cells for protein production. High Five insect cells (InVitrogen, San Diego, Calif.) (1.5× 10⁶ cells/ml) were infected with approximately 1×10⁷ viral particles/ml of the recombinant virus. After 48 hours, the culture supernatant was collected by centrifugation at 5,000×g for 30 minutes. The supernatant was then applied to a lysine-Sepharose column and Angiostatin protein eluted with ε-aminocaproic acid as previously described (Wu, Z., et. al., (1997) *Biochem. Biophys. Res. Commun.* 236:651–654).

Recombinant K5 of human plasminogen was produced by the following procedure: The CDNA for K4–5 was amplified from HPg cDNA template by PCR as previously described (Menhart, N., et. al., (1993) *Biochemistry* 32:8799–8806). The amplified cDNA was inserted between the Avr II and the Not I sites of the pPIC9K vector (InVitrogen, San Diego, Calif.). The transfer plasmid, pPIC9K[K4–K5 of HPg], was then linearized with restriction endonuclease Sac I and transformed into the KM71 strain of *Pichia pastoris* by electroporation. Isolation of high-yield clones and the following high bio-mass fermentation were performed as previously described (Nilsen, S. L., et. al., (1997) *Biotech. and Applied Biochem.* 25:63–74). The K4–K5 protein of human plasminogen was purified from the fermentation medium by lysine affinity chromatography as described (Chang, Y., et. al., (1997) *Biochemistry* 36(25):7652–7663). The purified products were extensively dialyzed against water, lyophilized, and digested with elastase at room temperature for 16 hours in 0.1 M phosphate/15 mM ε-aminocaproic acid (pH 7.8) at a protein: elastase ratio of 1:250 (w/w). The digest was then reapplied to a lysine-Sepharose chromatography column and the kringle 5 fragment collected in the flow-through. The kringle 5 protein was extensively dialyzed against water and lyophilized.

Additionally, the inventors have generated recombinant K5 clones in a Bacculovirus expression system. The pMelBac A vector was selected because of its smaller size (4.8 kb) for easier cloning and its honeybee melittin signal sequence for efficient secretion of recombinant protein. The K5 cDNA was PCR amplified using the following primers:

```
5'-GCG GAT CGA TGG GGA TCC GAA GAA
   GAC TGT ATG                         (SEQ ID NO:4)
```

(forward primer containing Bam HI restriction site and the 5'-end sequence of K5), and

```
5'-GTA CCA GCT GCA GAT CTC GAG CTA CTA AGG GGC
   CGC ACA CTG                         (SEQ ID NO: 5)
```

(reverse primer containing a Xho I restriction site and the 3'-end sequence of K5). The PCR-amplified K5 cDNA product is then cloned into a pMelBac A vector via homologous recombination as known in the art.

Similar methods were followed in order to manufacture a K1–5 molecule, using the following primers (available from Gibco BRL):

```
5'-CCT CCT CTT CAG CAG AGT CGA CTC CAA GCT TTA
   CTA AGG GGC CGC ACA CTG AGG GAC  (SEQ ID NO:6);

5'-GTA TAC ATT TCT TAC ATC TAT GCG GAT CGA TGG
   GGA TCC GAG CCT CTG GAT GAC TAT GTG
   AAT ACC                              (SEQ ID NO:7);
``` and

```
5'-GTA TAC ATT TCT TAC ATC TAT GCG GAT CGA TGG
   GGA TCC TTA TTT GAA AAG AAA GTG TAT CTC TCA
   GAG                                  (SEQ ID NO: 8).
```

Two molecular constructs comprising both K1–5 and K1–5 plus the PAD were generated. As compared with K1–5, the PAD-K1–5 construct contains an additional pre-activation domain, an upstream region consisting of the first 77 amino acid residues of plasminogen (FIG. 1). The PAD is known to stabilize plasminogen as a zymogen. During plasminogen activation to plasmin, PAD is proteolytically cleaved off from the plasminogen template.

EXAMPLE 2

Anti-Endothelial Cell Proliferative/Migratory Activity Comparison of AST, K1–5, K5 and PAD-K1–5

Assays measuring anti-endothelial cell activity were run according to Ji, et al., (1998) *Biochem. Biophys. Res. Commun.* 247:414–419; and Ji, et al., (1998) *FASEB Jrnl* 12(15):1731–1738. The inventors compared the inhibitory activities of PAD-K1–5, Angiostatin (K1–4), and K5 on endothelial cell migration. Both Angiostatin and K5 blocked endothelial cell migration with IC50 values of approximately 539.2 nM and 675.6 nM, respectively. (See FIG. 2). In comparison, PAD-K1–5 produced 50% of inhibition of endothelial cell migration at a dose of approximately 20.0 nM, suggesting that PAD-K1–5 is markedly more potent than either Angiostatin or K5. As summarized in Table 1 below, PAD-K1–5 is an efficacious anti-migratory agent with an IC50 value of 20.0 nM, an IC75 value of 198.1 nM, and an IC90 value of 699.5 nM, respectively. In contrast, K1–5 lacking the PAD is much less potent with an IC50 value of 87.5 nM, and IC75 and IC90 values of more than 1,000 nM.

TABLE 1

Comparison of inhibitory activities of endothelial cell migration between recombinant PAD-K1-5 and K1-5 of human plasminogen (*P-value < 0.01)

| Samples | IC50 (nM) | IC75 (nM) | IC90 (nM) |
|---|---|---|---|
| K1-5 | 87.5 +/− 42.7 | >1,000 | >1,000 |
| PAD-K1-5 | 19.9 +/− 15.8 | 198.1 +/− 99.4* | 699.5 +/− 148.2* |

These observations show that the presence of PAD significantly enhances the anti-migratory activities of K1–5, or any other combination of kringle domains. Since endothelial cell migration is an integral step in angiogenesis, the PAD-K molecules disclosed herein are novel angiogenesis inhibitors, and may be useful in the treatment of cancer, diabetic retinopathy, rheumatoid arthritis, psoriasis, atherosclerotic plaque formation, and any process that involves angiogenesis. Moreover, the process disclosed herein of manufacturing an anti-angiogenic compound comprising at least one kringle region from plasminogen by associating said at least one kringle region of plasminogen with the PAD from plasminogen is novel, and provides those skilled in the art with a method of recombinantly manufacturing a stable anti-angiogenic compound.

Although the present invention has been described in some detail by way of illustration and example for purposes of clarity and understanding, it will be apparent that certain changes and modifications may be practiced within the scope of the appended claims.

We claim:

1. An anti-angiogenic composition comprising a purified polypeptide the amino acid sequence of which comprises the pre-activation domain from plasminogen and at least one kringle from plasminogen, wherein said pre-activation domain comprises amino acid residues 1–77 of SEQ ID NO: 1.

2. The composition of claim 1 wherein said pre-activation domain and said kringle are derived from the same or different species.

3. The composition of claim 2 wherein said pre-activation domain and said kringle are derived from the group consisting of murine plasminogen, human plasminogen, Rhesus plasminogen, porcine plasminogen, canine plasminogen and bovine plasminogen.

4. An anti-angiogenic therapeutic composition comprising a purified polypeptide the amino acid sequence of which comprises the pre-activation domain from plasminogen, at least one kringle from plasminogen and a pharmaceutically acceptable carrier, wherein said pre-activation domain comprises amino acid residues 1–77 of SEQ ID NO: 1.

5. The therapeutic composition of claim 4 wherein said pre-activation domain and said kringle are derived from the same or different species.

6. The therapeutic composition of claim 5, wherein said pre-activation domain and said kringle are derived from the group consisting of murine plasminogen, human plasminogen, Rhesus plasminogen, porcine plasminogen, canine plasminogen and bovine plasminogen.

7. A method for inhibiting angiogenesis comprising administering to an endothelial cell an amount effective to inhibit cell proliferation or migration of a composition comprising a purified polypeptide the amino acid sequence of which comprises the pre-activation domain from plasminogen and at least one kringle from plasminogen, wherein said pre-activation domain comprises amino acid residues 1–77 of SEQ ID NO: 1.

8. The method of claim 7 wherein said pre-activation domain and said kringle are derived from the same or different species.

9. The method of claim 5 wherein said pre-activation domain and said kringle are derived from the group consisting of murine plasminogen, human plasminogen, Rhesus plasminogen, porcine plasminogen, canine plasminogen and bovine plasminogen.

* * * * *